US 6,632,953 B1

(12) United States Patent
Stürmer et al.

(10) Patent No.: US 6,632,953 B1
(45) Date of Patent: Oct. 14, 2003

(54) PRODUCTION OF OPTICALLY ACTIVE PHOSPHOLANES

(75) Inventors: Rainer Stürmer, Rödersheim-Gronau (DE); Armin Börner, Rostock (DE); Jens Holz, Rostock (DE); Gudrun Voss, Rostock (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/700,521

(22) PCT Filed: May 28, 1999

(86) PCT No.: PCT/EP99/03702

§ 371 (c)(1),
(2), (4) Date: Nov. 15, 2000

(87) PCT Pub. No.: WO99/62917

PCT Pub. Date: Dec. 9, 1999

(30) Foreign Application Priority Data

May 29, 1998 (DE) .......................................... 198 24 121

(51) Int. Cl.$^7$ ................................................ C07F 9/535
(52) U.S. Cl. .......................................... 556/13; 568/12
(58) Field of Search ............................... 556/13, 21, 17; 568/8, 12

(56) References Cited

U.S. PATENT DOCUMENTS

| 3,803,225 A | * | 4/1974 | Smith et al. | |
|---|---|---|---|---|
| 5,008,457 A | | 4/1991 | Burk | |
| 6,043,396 A | * | 3/2000 | Sturmer et al. | ................ 568/12 |

FOREIGN PATENT DOCUMENTS

| EP | 151 272 | 8/1985 |
|---|---|---|
| EP | 185 882 | 7/1986 |
| EP | 269 395 | 6/1988 |
| EP | 271 311 | 6/1988 |
| EP | 614 901 | 9/1994 |
| EP | 889 048 | 1/1999 |
| WO | 91/17998 | 12/1991 |
| WO | 92/19636 | 12/1992 |
| WO | 93/19040 | 9/1993 |

OTHER PUBLICATIONS

Tetrahedron Letters by Holz et al 40 (39) pp 7059–7062 Sep. 1999.*
J.Am.Chem.Soc.1996, 118, 5142–5143, Burk et al.
J.Am.Chem.Soc.1993, 115, 10125–10138,Burk et al.
J.Am.Chem.Soc.1995, 117, 9375–9376,Burk et al. 74.
Asymmetry vol. 2, No. 7,569–592, 1991, Burk et al.
J.Org. Chem., 328(1987) 71–80, Brunner et al.
Chiral Ligands for Asymmetric Catalysis, pp. 13–23
Acc.Chem.Res. 1990,23,345–350,Takaya.
J.Am.Chem.Soc., Oct. 23, 1991,No. 22, vol. 113, 8518–8519.

* cited by examiner

Primary Examiner—Jean F. Vollano
(74) Attorney, Agent, or Firm—Keil & Weinkauf

(57) ABSTRACT

Phospolanes and diphospholanes of the general formula I

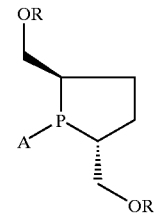

where:
   is H, $C_1$–$C_6$-aryl, alkylaryl, $SiR_3^2$,
$R^2$ is alkyl or aryl,
A is H, $C_1$–$C_6$-alkyl, aryl, Cl or

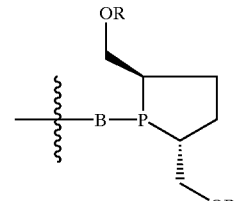

B is a linker with 1–5 C atoms between the two P atoms, and their use as catalyst in asymmetric synthesis.

8 Claims, No Drawings

PRODUCTION OF OPTICALLY ACTIVE PHOSPHOLANES

This application is a 371 of PCT/E99/03702 filed May 28, 1999, now WO 99/62917.

The invention describes novel optically active phospholanes and bisphospholanes, the preparation thereof and use thereof as ligands in metal complexes, and the use of the metal complexes for enantioselective synthesis.

Enantioselective hydrogenation and isomerization with rhodium and ruthenium complexes is very important in the synthesis of optically active compounds (e.g. Tani et al. J. Am. Chem Soc 106, 5211, 1984; R. Noyori, Acc. Chem. Res. 23, 345 (1990). The stoichiometric starting material hydrogen costs little, but the catalysts employed, which are mostly prepared from an optically active diphosphine ligand and a rhodium or ruthenium compound, are very costly and can be obtained only in a complicated manner.

The known methods for preparing optically active phosphines and diphosphines are all complicated and usually include a technically elaborate and costly racemate resolution (e.g. EP-A 0614901; EP-A 0271311; H. B. Kagan, "Chiral Ligands for Asymmetric Catalysis" in Asymmetric Synthesis, Vol. 5 (1985), pages 13–23, EP-A 0151282; EP-A 0185882; R. Noyori, Acc. Chem. Res. 23, 345 (1990); EP-269395; M. J. Burk, Tetrahedron, Asymmetry, pages 569–592 (1991); J. Am. Chem. Soc. 113, pages 8518–9 (1991), ibid. 115, pages 10125–138 (1993), ibid. 117, pages 9375–76 (1995), ibid 118, page 5142 (1996)). These disadvantages make industrial use difficult and uneconomic.

It is an object of the present invention to provide phosphine ligands which can be prepared easily and at low cost and which are good ligands for metal complex catalysts for enantioselective synthesis.

We have found that this object is achieved by a particularly efficient class of ligands, mainly phospholanes, which can be obtained from the "chiral pool". The starting material is in this case mannitol and other carbohydrates which can be obtained in large quantities at low cost.

The resulting phospholanes and diphospholanes provide excellent enantiomeric excesses in asymmetric hydrogenations. The known DUPHOS ligands of Burk et al. (M. J. Burk, Tetrahedron, Asymmetry, pages 569–592 (1991); J. Am. Chem. Soc. 113, pages 8518–9 (1991), ibid. 115, pages 10125–138 (1993), ibid. 117, pages 9375–76 (1995), ibid 118, page 5142 (1996); U.S. Pat. No. 5,008,457; WO 92/19630; WO 93/19040) are very much more elaborate to synthesize, in contrast to the present invention. Synthesis of the DUPHOS ligands requires, inter alia, an impractical electrolytic Kolbe synthesis in addition to an asymmetric hydrogenation.

The present invention avoids these difficulties by using the sugar mannitol which can be obtained enantiomerically pure from natural sources. In addition, this precursor provides a route to compounds which have alkoxymethyl or hydroxymethyl groups in positions 2 and 5 in the phospholane ring. Compounds of this type cannot be prepared by the known DUPHOS synthesis.

The invention relates to phospholanes and diphospholanes of the general formula I

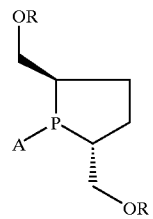

where:
R is H, $C_1$–$C_6$-alkyl, aryl, alkylaryl, $SiR_3^2$,
$R^2$ is alkyl or aryl,
A is H, $C_1$–$C_6$-alkyl, aryl, Cl or

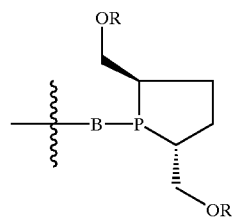

B is a linker with 1–5 C atoms between the two P atoms.

Preferred substituents R are hydrogen, methyl, ethyl, n-propyl, isopropyl, n-butyl, isobutyl, tert-butyl, benzyl, trityl and trialkylsilyl or triarylsilyl ($SiR_3^2$ where $R^2$=$C_1$–$C_6$-alkyl or aryl).

In the case of the diphospholanes, those which are preferred have

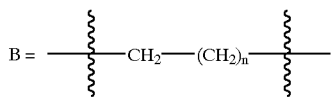

with n=0, 1, 2, 3, 4

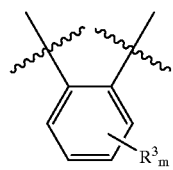

Particularly preferred linkers B are those where n is 1 or 2 and m is 0.

The invention further relates to metal complexes comprising the abovementioned phospholanes with central atoms from the group of Rh, Ru, Ir, Pd, Pt, Ni.

Particularly preferred metal complexes are those which contain ruthenium or rhodium as central atom.

These complexes can be prepared by synthesizing the catalytically active complexes in a known manner (e.g. Uson, Inorg. Chim. Acta 73, 275 (1983), EP-A 0158875, EP-A 437690) by reacting with rhodium, iridium, ruthenium, palladium, platinum or nickel complexes which contain labile ligands (e.g. $[RuCl_2(COD)]_n$, $Rh(COD)_2BF_4$, $Rh(COD)_2ClO_4$, $[Ir(COD)Cl]_2$, p-cymene-ruthenium chloride dimer).

The invention further relates to the use of these metal complexes in asymmetric synthesis, especially as catalyst for hydrogenations, hydroformylations, hydrocyanations, allylic substitutions and isomerizations of allylamines to enamines.

These reactions can be carried out with the metal complexes according to the invention under conditions familiar to the skilled worker.

The hydrogenation with the metal complexes according to the invention is usually carried out at a temperature from −20 to 150° C., preferably at 0 to 100° C. and particularly preferably at 15 to 40° C.

The pressure of hydrogen for the hydrogenation process according to the invention can be varied in a wide range between 0.1 bar and 300 bar. Very good results are obtained with a pressure in the range from 1 to 10, preferably 1 to 2 bar.

It is particularly advantageous with the ligands according to the invention that the hydrogenations can be carried out very efficiently at the low pressure of 1 to 2 bar of hydrogen.

Preferred solvents for the hydrogenations are $C_1$–$C_4$-alkanols, especially MeOH. In the case of substrates of low solubility, solvent mixtures, e.g. methanol and $CH_2Cl_2$ or THF, toluene are also suitable.

The catalyst is normally employed in amounts of from 0.001 to 5 mol %, preferably 0.001 to 0.01 mol %, based on the substrate to be hydrogenated.

EXAMPLE 1

Experimental Part

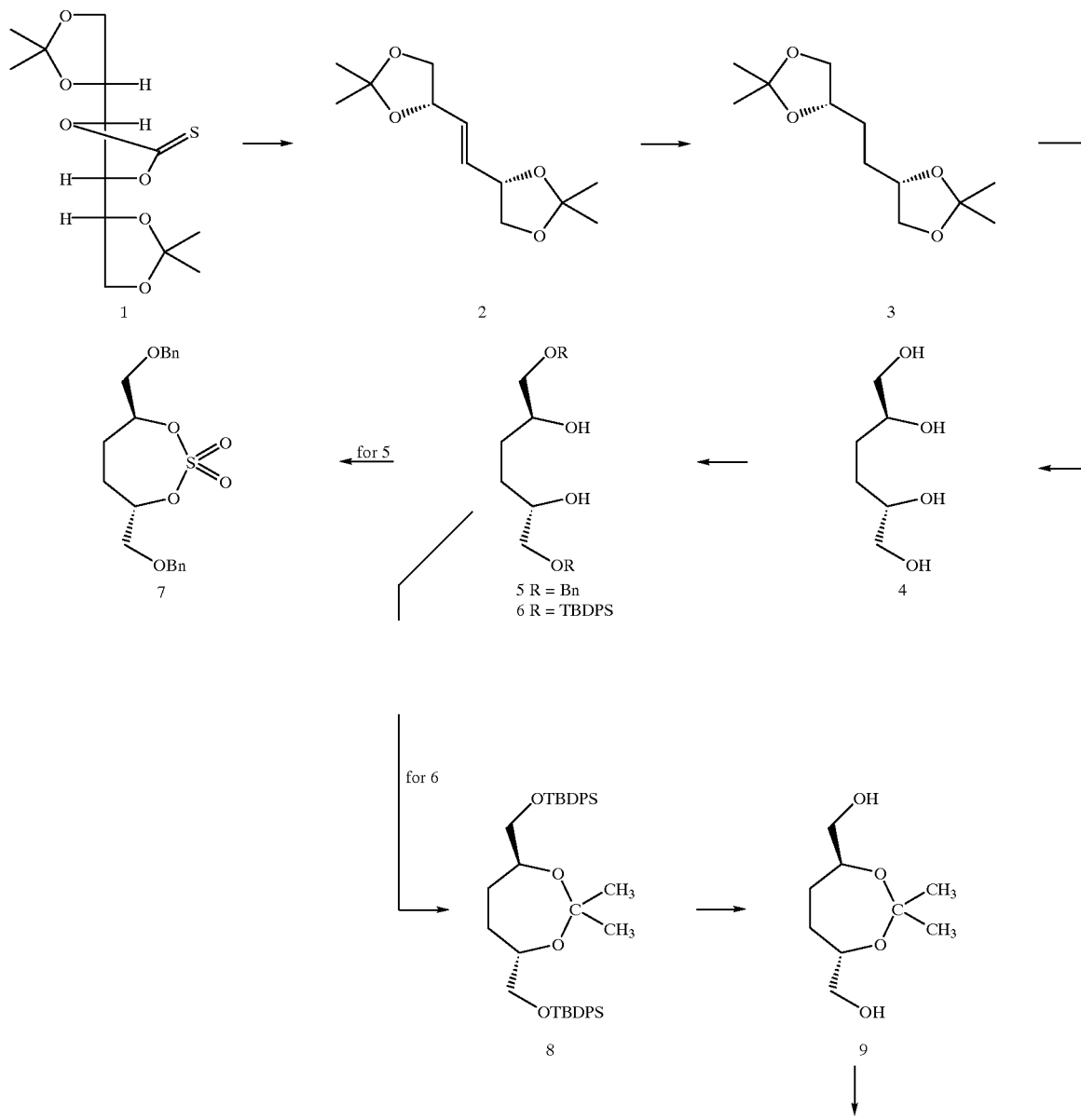

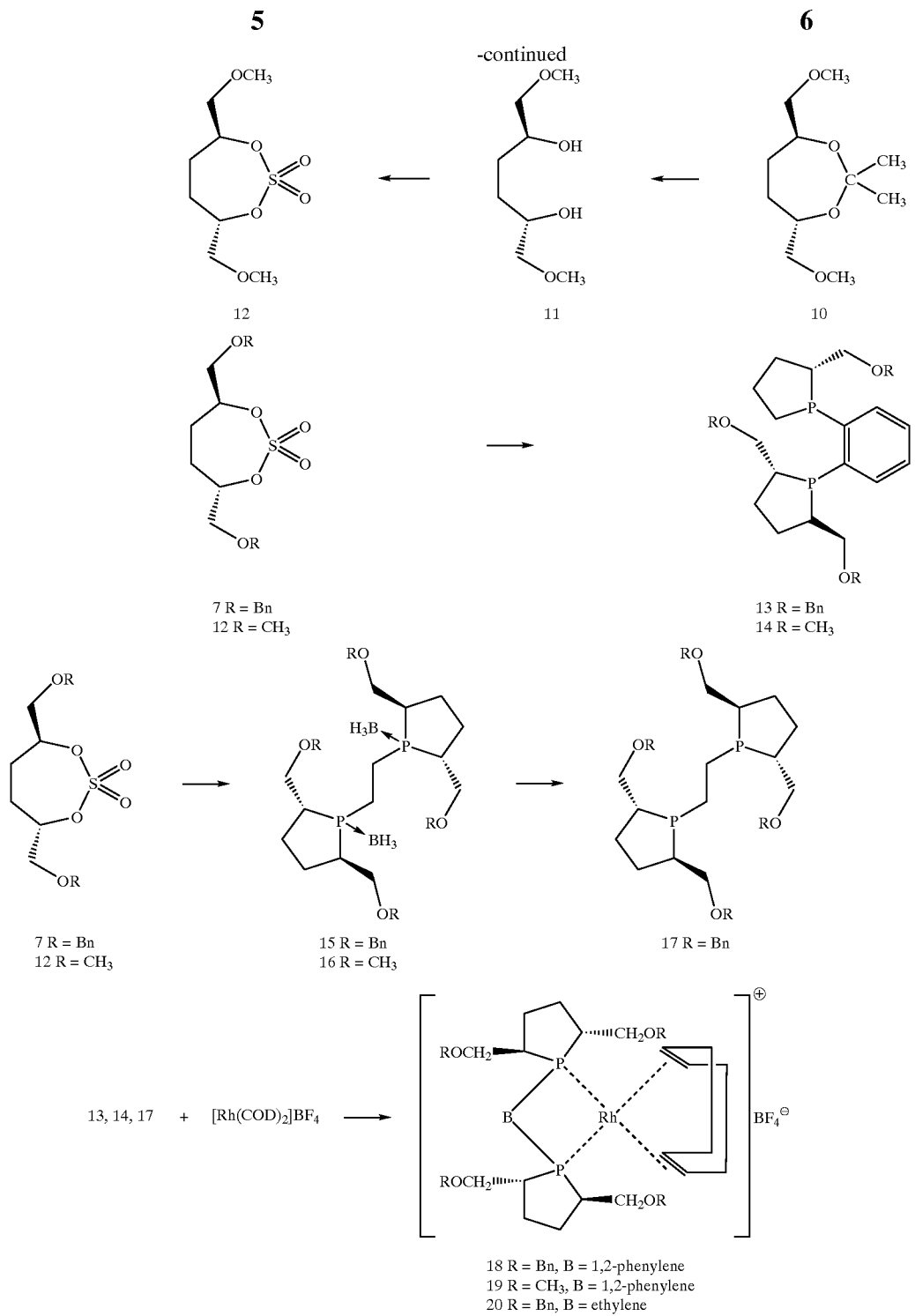

7 R = Bn
12 R = CH$_3$

13 R = Bn
14 R = CH$_3$

7 R = Bn
12 R = CH$_3$

15 R = Bn
16 R = CH$_3$

17 R = Bn 13, 14, 17 + [Rh(COD)$_2$]BF$_4$ →

18 R = Bn, B = 1,2-phenylene
19 R = CH$_3$, B = 1,2-phenylene
20 R = Bn, B = ethylene The method of E. J. Corey et al.[1] was used to react 1,2;5,6-di-O-isopropylidene-D-mannitol with thiophosgene in the presence of 4-dimethylaminopyridine in methylene chloride with a yield of 90%.

E-3,4-Didehydro-3,4-dideoxy-1,2;5,6-di-O-isopropylidene-D-threo-hexitol (2)

Heating the cyclic thiocarbonate 1 in triethyl phosphite for 20 hours in accordance with the literature[2,3] resulted in the trans-olefin in yields of 80 to 90%.

3,4-Dideoxy-1,2;5,6-di-O-isopropylidene-D-threo-hexitol (3)

In a modification of the method of Machinaga et al.[4], the olefin 2 (10 g) was hydrogenated in methanol with 10% platinum on active carbon (250 mg) under atmospheric pressure to give compound 3. After purification by column chromatography, the yield was 80 to 90%. Compound 3 can also be purified by distillation in accordance with the literature[4] (boiling point 0.6 mm=73° C.).

3,4-Dideoxy-D-threo-hexitol (4)

Acid hydrolysis of the isopropylidene groups took place in 1N hydrochloric acid in accordance with the literature[4]. The compound was obtained in a yield of 85% after recrystallization.

(2S,5S)-1,6-Bis(benzyloxy)-2,5-hexanediol (5)

3.0 g (20 mmol) of 3,4-dideoxy-D-threo-hexitol (4) was converted by the method of Marzi et al.[5] into 3.70 g of the 1,6-di-O-benzylated product 5 in a yield of 56%.

(2S,5S)-1,6-Bis(tert-butyldiphenylsilyloxy)-2,5-hexanediol (6)

3.0 g (20 mmol) of compound 4 were reacted with tert-butyldiphenylchlorosilane in DMF in the presence of imidazole based on the literature[5] gives the derivative 6 in a yield of 80%.

(4S,7S)-4,7-Bis(benzyloxymethyl)-2,2-dioxo[1,3,2]dioxathiepane (7)

1.43 g (12 mmol) of thionyl chloride were slowly added to 3.30 g (10 mmol) of the diol 5 in 70 ml of dry tetrachloromethane under an argon atmosphere, and the mixture was then refluxed for 90 minutes. After removal of the solvent in a rotary evaporator, the residue was taken up in a mixture of tetrachloromethane (40 ml), acetonitrile (40 ml) and water (60 ml) and, at 0° C., 15 mg (72 μmol) of $RuCl_3*3H_2O$ and 4.28 g (20 mmol) of sodium periodate were added. The mixture was then left to stir at room temperature for one hour, and then 50 ml of water were added to the suspension. Subsequent extraction with diethyl ether (3×75 ml) and washing of the organic phase with saturated NaCl solution (100 ml), followed by drying ($Na_2SO_4$), resulted in a residue which on column chromatography (n-hexane:AcOEt=2:1, $R_f$=0.20) afforded compound 7 in a yield of 3.37 g (86%).

Melting point=57 to 59° C.; $[\alpha]D^{26}$=−37.2° (c 1.01; $CHCl_3$); $^1$H-NMR ($CDCl_3$, 400 MHz) δ7.34 (10H, m, arom. H), 4.78 (2H, m, H-2/5), 4.57 (2H, AB sp., $H_a$-$CH_2$Ph, $^2J_{a,b}$=12.0 Hz) , 4.56 (2H, AB sp., $H_b$-$CH_2$Ph, $^2J_{a,b}$=12.0 Hz), 3.65 (2H, dd, $H_a$-$CH_2$OH, $^2J_{a,b}$=10.8 Hz, $^3J_{H,H}$=5.4 Hz), 3.56 (2H, dd, $H_b$-$CH_2$OH, $^2J_{a,b}$=10.8 Hz, $^3J_{H,H}$=4.9 Hz), 2.00 (4H, m, H-3/4); $^{13}$C-NMR ($CDCl_3$, 100 MHz) δ137.3, 128.4–127.7 (arom. C), 82.6 (C-2/5), 73.4 ($CH_2$Ph), 70.8 (C-1/6), 28.9 (C-3/4); elemental analysis $C_{20}H_{24}O_6S$ (392.47) calc.: C, 61.21; H, 6.16; S, 8.17; found: C, 61.03; H 6.19; S 8.10;

1,6-Di-O-(tert-butyldiphenylsilyl)-2,5-O-isopropylidene-3,4-dideoxy-D-threo-hexitol (8)

6.27 g (10 mmol) of compound 6 were converted into the isopropylidene derivative 8 in a yield of 85% (5.67 g) in accordance with the literature[5]. 8 was purified for characterization by column chromatography (n-hexane: diethyl ether=19:1, $R_f$=0.2). Purification of the compound was unnecessary for the next reaction step.

2,5-O-Isopropylidene-3,4-dideoxy-D-threo-hexitol (9)

Elimination of the silyl groups from 6.67 g (10 mmol) of the silyl compound 8 with tetrabutylammonium fluoride in THF[5] and subsequent purification by chromatography (diethyl ether:MeOH=19:1, $R_f$=0.5) resulted in 1.7 g (89%) of diol 9.

2,5-O-Isopropylidene-1,6-di-O-methyl-3,4-dideoxy-D-threo-hexitol (10)

A solution of 3.80 g (20 mmol) of the diol 9 in 30 ml of THF was added at 0° C. to a solution of 1,06 g (44 mmol) of NaH in 60 ml of THF. After the alcoholate formation was complete, 2.2 equivalents of methyl iodide (6.21 g, 44 mmol) were slowly added, and the mixture was stirred at room temperature. After completion of the reaction, the excess NaH was cautiously destroyed with water (30 ml), and the THF was removed in vacuo. The remaining aqueous solution was then extracted with methylene chloride (3×50 ml), and the combined organic phase was dried ($Na_2SO_4$). The residue obtained after concentration afforded, after column chromatography (n-hexane:AcOEt=2:1, $R_f$=0.40), a colorless syrup in a yield of 84% (3.68 g).

Syrup; $[\alpha]D^{23}$=−32.8° (c 1.01, $CHCl_3$); $^1$H-NMR ($CDCl_3$, 400 MHz) δ3.92 (2H, m, H-2/5), 3.32 (2H, dd, $H_a$-$CH_2$O, $^2J_{a,b}$=9.9 Hz, $^3J^{H,H}$=6.3 Hz), 3.30 (6H, s, $CH_3$), 3.55 (2H, m, $H_b$-$CH_2$O, $^2J_{a,b}$=9.9 Hz, $^3J_{H,H}$=5.3 Hz), 1.67 (2H, m, $H_a$-3/4), 1.34 (2H, m, $H_b$-3/4), 1.31 (6H, s, $CH_3$); $^{13}$C-NMR ($CDCl_3$, 100 MHz) δ100.5 ($C(O)_2$), 76.2 (C-1/6), 70.4 (C-2/5), 59.1 ($CH_3$), 31.1 (C-3/4), 25.6 ($C(CH_3)_2$); elemental analysis $C_{11}H_{22}O_4$ (218.293) calc.: C, 60.52; H, 10.16; found: C, 60.38; H, 10.07;

(2S,5S)-1,6-Bis(benzyloxy)-2,5-hexanediol (11)

4.0 g (18.32 mmol) of compound 10 were hydrolyzed in a mixture of 60 ml of THF and 60 ml of 1N hydrochloric acid in 20 minutes. After the solution had been concentrated in a rotary evaporator it is chromatographed (EtOH:AcOEt= 1:3, $R_f$=0.45) to result in 3.20 g of a pale yellow syrup 11 in almost quantitative yield.

Syrup; $[\alpha]D^{22}$=−7.2° (c 1.09, $CH_3OH$); $^1$H-NMR ($CD_3OD$, 400 MHz) δ3.72 (2H, m, H-2/5), 3.37 (6H, s, $CH_3$), 3.38–3.30 (4H, m, $CH_2OH$), 1.56 (4H, m, H-3/4); $^{13}$C-NMR ($CD_3OD$, 100 MHz) δ78.2 (C-1/6), 70.1 (C-2/5), 59.2 ($CH_3$), 30.6 (C-3/4); elemental analysis $C_8H_{18}O_4$ (178.228) calc.: C, 53.91; H, 10.18; found: C, 53.47; H, 10.14;

(4S,7S)-4,7-Bis(methyloxymethyl)-2,2-dioxo[1,3,2]dioxathiepane (12)

1.78 g (10 mmol) of the diol 11 were converted into the target compound 12 in analogy to the preparation of the cyclic sulfate 7. It was possible to dispense with purification by chromatography (n-hexane:AcOEt=1:2, $R_f$=0.4) in this case because the product 12 could be isolated by crystallization from diethyl ether/n-hexane as a white solid in a yield of 76% (1.83 g).

Melting point=75–78° C.; $[\alpha]D^{23}$=−44.1° (c 1.01; $CHCl_3$); $^1$H-NMR ($CDCl_3$, 400 MHz) δ4.72 (2H, m, H-2/5), 3.56 (2H, dd, $H_a$-$CH_2$O, $^2J_{a,b}$=10.8 Hz, $^3J_{H,H}$=5.4 Hz), 3.47 (2H, dd, $H_a$-$CH_2$O, $^2J_{a,b}$=10.8 Hz, $^3J_{H,H}$=4.7 Hz), 3.37 (6H, s, $CH_3$), 2.04–1.92 (4H, m, H-3/4); $^{13}$C-NMR ($CDCl_3$, 100 MHz) δ82.5 (C-2/5), 73.4 (C-1/6), 59.3 ($OCH_3$), 28.8 (C-3/4); elemental analysis $C_8H_{16}O_6S$ (240.274) calc.: C, 39.99; H, 6.71; S, 13.34; found: C, 40.06; H, 6.76; S, 1.27;

1,2-Bis[(2R,5R)-2,5-benzyloxymethylphospholanyl]benzene(13)

2.0 equivalents of n-BuLi (4.58 ml, 1.6 M solution in n-hexane) were slowly added to 0.52 g (3.66 mmol) of 1,2-bis(phosphinyl)-benzene in 50 ml of THF and, after 2 hours, 2.86 g (7.32 mmol) of the cyclic sulfate 7 in 20 ml of THF were added slowly to the resulting yellow solution. The mixture was stirred at room temperature for a further 2 hours and, finally, 2.2 equivalents of n-BuLi (5.03 ml, 1.6 M solution in n-hexane) were again added. The solution was stirred overnight, and excess BuLi was finally destroyed with 2 ml of MeOH. The solvent was removed in vacuo, and the residue was taken up with 20 ml of water under anaerobic conditions and then extracted with methylene chloride (2×50 ml). After drying the organic phase ($Na_2SO_4$) and removing the solvent, the required product was isolated by column chromatography (n-hexane:AcOEt=4:1, $R_f$=0.35) in a yield of 0.52 g (19%) as a pale yellow syrup.

Syrup; $^1$H-NMR ($CDCl_3$, 400 MHz) δ7.45–7.10 (24H, m, arom. H), 4.49 (2H, AB sp., $H_a$-$CH_2$Ph, $^2J_{a,b}$=12.1 Hz), 4.47 (2H, AB sp., $H_b$-$CH_2$Ph, $^2J_{a,b}$=12.1 Hz), 4.18 (2H, AB sp., $H_a$-$CH_2$Ph, $^2J_{a,b}$=11.9 Hz), 4.04 (2H, AB sp., $H_b$-$CH_2$Ph, $^2J_{a,b}$=11.9 Hz), 3.65–3.45 (4H, m, CH$_2$O), 2.97–2.80 (4H, m, CH$_2$O), 2.70 (2H, m, CH-P); 2.33 (4H, m, CH-P, H$_a$-(CH$_2$)$_2$); 2.18 (2H, m, H$_a$-(CH$_2$)$_2$), 1.80–1.53 (4H, m, H$_b$-(CH$_2$)$_2$); $^{13}$C-NMR (CDCl$_3$, 100 MHz) δ141.8 (m, C$_{ar}$-P), 138.6+138.5 (ipso-C), 131.8, 128.4–127.1 (arom. C), 74.1 (m, CH$_2$Ph), 73.0 (CH$_2$Ph), 72.5 (CH$_2$O), 72.5 (CH$_2$O), 39.5 (CH-P), 38.9 (m, CH-P), 30.9 (CH$_2$), 30.4 (CH$_2$); $^{31}$P-NMR (CDCl$_3$, 162 MHz) δ11.5;

1,2-Bis[(2R,5R)-2,5-methyloxymethylphospholanyl]benzene(14)

In analogy to the preparation of bisphospholane 13, the compound 12 was reacted in place of the cyclic sulfate 7 to give the required methoxymethyl-substituted bisphospholane 14. Purification and isolation took place by column chromatography (n-hexane:AcOEt=2:1, R$_f$=0.20) in a yield of 0.80 g (48%) of the colorless syrup.

Syrup; $^1$H-NMR (CDCl$_3$, 400 MHz) δ7.45 (2H, m, arom. H), 7.30 (2H, m, arom. H), 3.55 (4H, m, CH$_2$O), 3.36 (2H, m, CH$_2$O), 3.35 (6H, s, CH$_3$), 3.10 (6H, s, CH$_3$), 2.90 (2H, m, CH$_2$O), 2.78 (2H, m, CH-P), 2.63 (2H, m, CH-P), 2.32 (2H, m, CH$_2$), 2.16 (4H, m, CH$_2$); 1.68 (2H, m, CH$_2$), 1.55 (4H, m, CH$_2$); $^{13}$C-NMR (CDCl$_3$, 100 MHz) δ141.9 (m, C$_{ar}$-P), 131.8, 128.4 (arom. C), 74.1 (m, CH$_2$Ph), 76.6 (m, CH$_2$O), 74.5 (CH$_2$O), 58.8 (CH$_3$), 58.2 (CH$_3$), 39.6 (CH-P), 39.0 (m, CH-P), 30.9 (CH$_2$), 30.3 (CH$_2$); $^{31}$P-NMR (CDCl$_3$, 162 MHz) δ–11.7;

1,2-Bis[(2R,5R)-2,5-benzyloxymethylphospholanyl]ethane borane complex (15)

7.40 mmol (4,63 ml) of a 1.6 M n-BuLi solution in hexane were added to 348 mg (3.70 mmol) of bis(phosphinyl)ethane in THF at room temperature, and the mixture was stirred for two hours. Then a solution of 2.90 g (7.40 mmol) of the cyclic sulfate 7 in 20 ml of THF was slowly added, and the mixture was stirred for a further two hours. Subsequent addition of a further 5.09 ml (8.14 mmol) of n-BuLi solution completed the reaction after stirring overnight. To form the borane adduct, the solution was cooled to –20° C. and 9.25 ml (9.25 mmol) of a 1M BH$_3$*THF solution were added. After two hours, excess BuLi and BH$_3$ were destroyed by adding 2 ml of MeOH, and the solvent was removed in vacuo. The residue was taken up in water and then extracted with methylene chloride. The extracts were then dried (Na$_2$SO$_4$) and concentrated, and the residue was purified by column chromatography (n-hexane: AcOEt=4:1, R$_f$=0.20). 350 mg (13%) of a viscous syrup were obtained.

Syrup; $^1$H-NMR (CDCl$_3$, 400 MHz) δ7.37–7.22 (20H, m, arom. H), 4.47 (2H, AB sp., H$_a$-CH$_2$Ph, $^2J_{a,b}$=11.2 Hz), 4.42 (2H, AB sp., H$_a$-CH$_2$Ph, $^2J_{a,b}$=12.1 Hz), 4.41 (2H, AB sp., H$_b$-CH$_2$Ph, $^2J_{a,b}$=12.1 Hz), 4.38 (2H, AB sp., H$_b$-CH$_2$Ph, $^2J_{a,b}$=11.2 Hz), 3.58 (4H, m, CH$_2$O), 3.43 (4H, m, CH$_2$O), 2.37 (2H, m, CH-P); 2.14–1.79 (10H, m, CH-P, (CH$_2$)$_2$), 1.41–1.20 (2H, m, (CH$_2$)$_2$), 0.85–0.00 (6H, m, BH$_3$); $^{13}$C-NMR (CDCl$_3$, 100 MHz) δ138.1+137.9 (ipso-C), 128.3–127.4 (arom. C), 73.2 (CH$_2$Ph), 72.7 (CH$_2$Ph), 69.4 (CH$_2$O), 68.4 (CH$_2$O), 39.5 (m, CH-P), 29.1 (CH$_2$), 28.6 (CH$_2$), 15.9 (m, (CH$_2$)$_2$); $^{31}$P-NMR (CDCl$_3$, 162 MHz) δ40.2;

1,2-Bis[(2R,5R)-2,5-methyloxymethylphospholanyl]ethane borane complex (16)

2.14 g (8.91 mmol) of cyclic sulfate 12 and 0.42 g (4.45 mmol) of bis(phosphinyl)ethane were reacted in analogy to the preparation of compound 15 to give the required borane-protected bisphospholane 16. Purification by chromatography took place with n-hexane:AcOEt=2:1 (R$_f$=0.15). A crystalline product was obtained in a yield of 0.71 g (39%).

Melting point=45–48° C.; [α]$_D^{23}$=21.9° (c 1.00; CHCl$_3$); $^1$H-NMR (CDCl$_3$, 400 MHz) δ3.51 (8H, m, CH$_2$O), 3.33 (6H, s, CH$_3$O), 3.32 (6H, m, CH$_3$O), 2.36 (2H, m, CH-P); 2.23–2.05 (6H, m, CH-P, (CH$_2$)$_2$), 1.96 (4H, m, CH$_2$)$_2$), 1.58–1.35 (4H, m, (CH$_2$)$_2$), 0.95–0.00 (6H, m, BH$_3$); $^{13}$C-NMR (CDCl$_3$, 100 MHz) δ71.6 (m, CH$_2$O), 70.8 (CH$_2$O), 58.7 (CH$_3$O), 58.7 (CH$_3$O), 39.5 (m, CH-P), 29.1 (CH$_2$), 28.9 (CH$_2$), 15.8 (m, (CH$_2$)$_2$); $^{31}$P-NMR (CDCl$_3$, 162 MHz): δ40.5; MS (m/z; EI) 391 [M$^+$-BH$_4$] (100);

1,2-Bis[(2R,5R)-2,5-methyloxymethylphospholanyl]ethane (17)

0.30 g (0.42 mmol) of the borane complex 15 were mixed with an anaerobic solution of 0.142 g (1.26 mmol) of DABCO in 6 ml of toluene and stirred at 40° C. After the reaction was complete, the solution was concentrated and purified by rapid column chromatography (n-hexane:AcOEt=4:1, R$_f$=0.55). The bisphospholane 17 was obtained in a yield of 0.21 g (73%) and was employed immediately for complex formation.

Syrup; $^1$H-NMR (CDCl$_3$, 400 MHz) δ7.35–7.21 (20H, m, arom. H), 4.52 (2H, AB sp., H$_a$-CH$_2$Ph, $^2J_{a,b}$=12.1 Hz), 4.48 (2H, AB sp., H$_b$-CH$_2$Ph, $^2J_{a,b}$=12.1 Hz), 4.43 (2H, AB sp., H$_a$-CH$_2$Ph, $^2J_{a,b}$=12.1 Hz), 4.41 (2H, AB sp., H$_b$-CH$_2$Ph, $^2J_{a,b}$=12.1 Hz), 3.61–3.41 (8H, m, CH$_2$O), 2.29 (2H, m, CH-P); 2.20 (2H, m, CH-P); 2.07 (4H, m, H$_a$-(CH$_2$)$_2$), 1.53–1.23 (8H, m, H$_b$-(CH$_2$)$_2$), (CH$_2$)$_2$); $^{13}$C-NMR (CDCl$_3$, 100 MHz) δ138.6+138.4 (ipso-C), 128.3–127.3 (arom. C), 74.2 (m, CH$_2$Ph), 72.9 (CH$_2$Ph), 72.7 (CH$_2$O), 70.2 (CH$_2$O), 43.7 (m, CH-P), 40.0 (m, CH-P), 31.4 (CH$_2$), 31.3 (CH$_2$), 19.1 (m, (CH$_2$)$_2$); $^{31}$P-NMR (CDCl$_3$, 162 MHz): δ–6.9;

Preparation of the [Rh(COD) (P-P)]BF$_4$ complexes 18, 19 and 20

0.3 mmol of the bisphospholane ligands 13, 14 and 17 were dissolved in 1.5 ml of THF and slowly added at a temperature of –10° C. to a suspension of 0.122 g (0.3 mmol) of [Rh(COD)$_2$]BF$_4$ in 3.5 ml of THF. After about 10 minutes, the solution was filtered under anaerobic conditions to remove insoluble constituents, and 15 ml of diethyl ether were added. This resulted in an orange precipitate or else a brown oil separating out. Decantation of the supernatant solution and washing twice with diethyl ether (5 ml) afforded, after drying in vacuo, an orange powder in NMR-spectroscopically pure form. [Rh(COD) (13)]BF$_4$ (18): Yield 225 mg (73%); $^1$H-NMR (CDCl$_3$, 400 MHz) δ7.70–6.80 (24H, m, arom. H), 5.76 (2H, m, CH$_{COD}$), 4.66 (2H, m, CH$_{COD}$), 4.42 (2H, AB sp., H$_a$-CH$_2$Ph, $^2J_{a,b}$=12.3 Hz), 4.18 (2H, AB sp., H$_b$-CH$_2$Ph, $^2J_{a,b}$=12.3 Hz), 4.05 (2H, AB sp., H$_a$-CH$_2$Ph, $^2J_{a,b}$=12.9 Hz), 4.05 (2H, AB sp., H$_b$-CH$_2$Ph, $^2J_{a,b}$=12.9 Hz), 3.80 (2H, m, CH$_2$O), 3.60 (4H, m, CH$_2$O), 3.30 (2H, m, CH$_2$O), 2.87–1.50 (20H, m, 4xCH-P, 4x(CH$_2$)$_2$); $^{13}$C-NMR (CDCl$_3$, 100 MHz) δ140.5 (m, Car-P), 137.7+137.0 (ipso-C), 132.3, 128.5–127.3 (arom. C), 107.0 (CH$_{COD}$), 91.9 (CH$_{COD}$), 73.2 (m, CH$_2$Ph), 73.0 (CH$_2$Ph), 70.6 (m, CH$_2$O), 68.1 (CH$_2$O), 49.7 (m, CH-P), 42.7 (m, CH-P), 33.7 (CH$_2$), 32.1 (CH$_2$), 31.3 (CH$_2$), 27.0 (CH$_2$); $^-$P-NMR (CDCl$_3$, 162 MHz): δ64.3 ($^1J_{Rh,P}$=150 Hz); MS (m/z; FAB$_{pos}$) 941 [M$^+$-BF$_4$] (20), 833 [M$^+$-BF$_4$-COD] (100);

[Rh(COD)(14)]BF$_4$ (19): Yield 155 mg (71%); $^1$H-NMR (CDCl$_3$, 400 MHz) δ7.74 (2H, m, arom. H), 7.68 (2H, m, arom. H), 5.57 (2H, m, CH$_{COD}$), 4.80 (2H, m, CH$_{COD}$), 3.82 (2H, m, CH$_2$), 3.67 (2H, m, CH$_2$), 3.50 (2H, m, CH$_2$), 3.26 (6H, s, CH$_3$O), 3.13 (2H, m, CH$_2$), 2.90 (2H, m, CH-P), 2.85 (6H, s, CH$_3$O), 2.67–2.27 (14 H, m, CH-P, (CH$_2$)$_2$), 1.94 (2H, m, (CH$_2$)$_2$), 1.58 (2H, m, (CH$_2$)$_2$);$^{13}$C-NMR (CDCl$_3$, 100 MHz) δ140.2 (m, C$_{ar}$-P), 132.4–132.0 (arom. C), 106.1 (m, CH$_{COD}$), 90.8 (m, CH$_{COD}$), 73.7 (m, CH$_2$O), 70.8 (CH$_2$O), 58.8+58.7 (CH$_3$O), 49.4+42.5 (m, CH-P), 33.5+31.9+31.2+27.6 (CH$_2$); $^{31}$P-NMR (CDCl$_3$, 162 MHz): δ65,0 ($^1J_{Rh,P}$=150 Hz);

[Rh(COD) (17)]BF$_4$ (20): Yield 190 mg (65%); $^1$H-NMR (CDCl$_3$, 400 MHz) δ7.30–7.05 (20H, m, arom. H), 5.55 (2H, m, CH$_{COD}$), 4.58 (2H, m, CH$_{COD}$), 4.43–4.20 (8H, m, CH$_2$Ph, 3.77–3.40 (8H, m, CH$_2$O), 2.50–1,90 (20H, m, CH-P, (CH$_2$)$_2$); 1.60–1.20 (4H, m, (CH$_2$)$_2$); $^{13}$C-NMR (CDCl$_3$, 100 MHz) δ137.9+137.7 (ipso-C), 128.5–127.2 (arom. C), 102.1 (CH$_{COD}$), 91.5 (CH$_{COD}$), 73.4+72.1 (CH$_2$Ph), 72.8 (CH$_2$O), 68.8 (CH$_2$O), 45.2+39.2 (m, CH-P), 32.7 (CH$_2$), 31.3 (CH$_2$), 30.0 (CH$_2$), 27.7 (CH$_2$) 20.8 (m, CH$_2$)$_2$); $^{31}$P-NMR (CDCl$_3$, 162 MHz): δ7. 3 ($^1J_{Rh,P}$=147 Hz);

References

[1] E. J. Corey; P. B. Hopkins *Tetrahedron Lett.* 23 (1982) 1979–1982;
[2] M. Marzi; D. Misiti *Tetrahedron Lett.* 30 (1989) 6075–6076;
[3] A. Haines *Carbohydrate Res.* 1 (1965) 214–228;
[4] N. Machinaga; C. Kibayashi *J. Org. Chem.* 57 (1992) 5178–5189;
[5] M. Marzi; P. Minetti; D. Misiti *Tetrahedron* 48 (1992) 10127–10132;

A is H, C$_1$–C$_6$-alkyl, aryl, Cl or

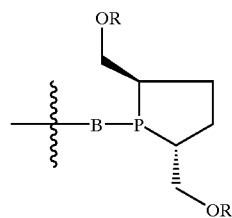

B is a linker with 1–5 C atoms between the two P atoms.

2. A phospholane as claimed in claim 1, where R is H or CH$_3$.

3. A diphospholane as claimed in claim 1, wherein the substituents have the following meaning:

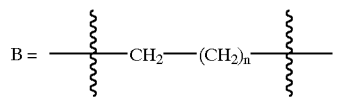

Results of the asymmetric hydrogenation of prochiral substrates
Conditions: Substrate: Catalyst = 100:1, MeOH, 25° C., 1 bar of H$_2$;

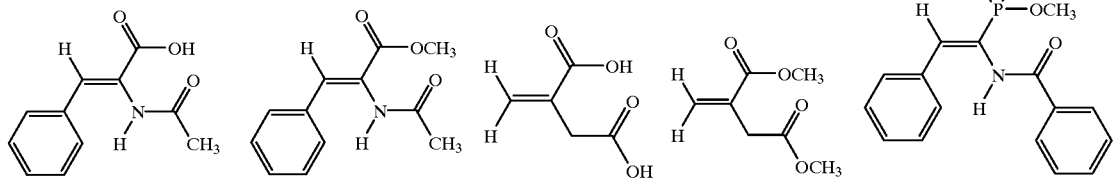

|    | $t_{100}$ | % ee | $t_{100}$ | % ee | $t_{100}$ | % ee | $t_{100}$ | % ee | $t_{100}$ | % ee |
|----|-----------|------|-----------|------|-----------|------|-----------|------|-----------|------|
| 18 | n.b.      | 73.8(S) | n.b.   | 72.2(S) | 3 h (98%) | 75.0(R) | 7 h (27%) | 9.2(S) | 48 h | 20.8(R) |
| 19 | 19 min    | 94.8(S) | 15 min | 98.9(S) | 20 min    | 96.9(R) | 3 h       | 97.2(R) | 4 h | 78.8(R) |
| 20 | 250 min   | 91.5(S) | 5 h    | 95.6(S) | 17 h (94%) | 81.5(R) | 19 h (63%) | 73.1(R) | 7 h | 71.9(R) |

We claim:

1. A phospholane or diphospholane of the general formula I

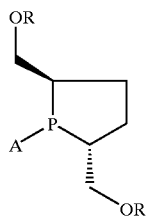

where:

R is H, C$_1$–C$_6$-alkyl, aryl, alkylaryl, SiR$_3^2$,
R$^2$ is alkyl or aryl, with n=0, 1, 2, 3, 4 or

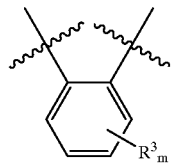

with m=0, 1, 2, 3
R$^3$=alkyl or fused aryl.

4. A diphospholane as claimed in claim 3, wherein the substituents have the following meaning:
m=0, n=1.

5. A metal complex comprising a phospholane as claimed in any of claim 1 and a central atom selected from the group of Rh, Ru, Ir, Pd, Pt, Ni.

6. A metal complex as claimed in claim 5, wherein Rh or Ru is selected as central atom.

7. A process for the asymmetric hydrogenation of compounds by reacting the starting compounds to be hydrogenated with hydrogen in the presence of a metal complex as claimed in claim 5.

8. A process as claimed in claim 7, wherein the hydrogenation is carried out under a pressure of from 1 to 2 bar of hydrogen.

* * * * *

UNITED STATES PATENT AND TRADEMARK OFFICE
CERTIFICATE OF CORRECTION

PATENT NO. : 6,632,953 B1 Page 1 of 1
DATED : October 14, 2003
INVENTOR(S) : Stuermer et al.

It is certified that error appears in the above-identified patent and that said Letters Patent is hereby corrected as shown below:

<u>Title page,</u>
Item [57], ABSTRACT,
Line 2, after formula I, insert -- R -- before "is H,".

<u>Column 13,</u>
Line 2, delete "any of".

Signed and Sealed this

Thirteenth Day of January, 2004

JON W. DUDAS
*Acting Director of the United States Patent and Trademark Office*